United States Patent [19]
Resnick et al.

[11] Patent Number: 5,324,830
[45] Date of Patent: Jun. 28, 1994

[54] CHIMERIC PROTEIN THAT HAS A HUMAN RHO MOTIF AND DEOXYRIBONUCLEASE ACTIVITY

[75] Inventors: Michael A. Resnick, Chapel Hill, N.C.; Terry Chow, Fleurimont, Canada; Ed Perkins, Carrborro, N.C.

[73] Assignee: United States of America, Washington, D.C.

[21] Appl. No.: 55,797

[22] Filed: Apr. 29, 1993

Related U.S. Application Data

[63] Continuation of Ser. No. 674,801, Mar. 26, 1991, abandoned.

[51] Int. Cl.$^5$ .................. C12N 15/53; C12N 1/15; C12N 9/22
[52] U.S. Cl. .................. 536/23.2; 435/199; 435/254.11
[58] Field of Search .............. 536/23.2; 435/199, 254

[56] References Cited

OTHER PUBLICATIONS

Chow, T. Y. K., et al. (1988) Mol. Gen. Genet. 211, 41–48.
Chow, T. Y. K., et al, (1987) J. Biol. Chem. 262(36), 17659–17667.
Suggs, S. V. et al. (1981) Proc. Natl. Acad. Sci. USA 78(11), 6613–6617.
Esposito, et al.; Current Genetics 1986 10:425–433; "The REC46 gene of Saccharomyces cerevisiae controls mitotic chromosomal stability, recombination and sporulation: cell-type and life cycle stage-specific expression of the rec46-1 mutation".
Kouprina, et al.; Yeast vol. 4:257–269 (1988); "Genetic Control of Chromosome Stability in the Yeast Saccharomyces cerevisiae".
Fitzgerald-Hayes, Molly; Yeast; vol. 3: 187–200 (1987); "Yeast Centromeres".
Rosenberg, S. and Hastings, P., "The split-end model for homologous recombination at double-strand breaks and at Chi," Biochimie 73:385–397 (1987).
Fraser, et al., "Neurospora Endo-Exonuclease Is Immunochemically Related to the recC Gene Product of Escherichia coli," J. Bacteriology 172-507–510 (1990).
Kunz, B. and Haynes R., "Phenomenology and Genetic Control of Mitotic Recombination in Yeast," Ann. Rev. Genet. 15:57–89 (1981).
Koa, H. et al., "Endo-exonuclease of Aspergillus nidulans," Biochem. Cell Biol. 68:387–392 (1989).
Dake, et al., "Purification and Properties of the Major Nuclease from Mitochondria of Saccharomyces cerevisiae," J. Biol. Chem 263:7691–7702 (1988).
Chardin, P. et al., "Coding Sequence of human rho cDNAs clone 6 and clone 9," Nucleic Acids Research 16:2717 (1988).
Yeramian, P. et al., "Nucleotide sequence of human rho cDNA clone 12" Nucleic Acids Research 15:1869 (1987).
Madaule, P. et al., "Characterization of two members of the rho gene family from the yeast Saccharomyces cerevisiae" Proc. Natl. Acad. Sci. USA 84:779–783 (1987).
Ramotar, D. et al., "Nuclear Endo-exonuclease of Neurospora crassa" J. Biol. Chem. 262:425–431 (1987).
Tomkinson, A. and Linn, S., "Purification and properties of a single strand-specific endonuclease from mouse cell mitochondria" Nucleic Acids Research 14:9579–9593 (1986).
Snyder, M. et al., "Rapid mapping of antigenic coding regions and constructing insertion mutations in yeast genes by mini-Tn10 transplason mutagenesis" Proc. Natl. Acad. Sci. USA 83:730–734 (1986).

(List continued on next page.)

Primary Examiner—Charles L. Patterson, Jr.
Attorney, Agent, or Firm—Knobbe, Martens, Olson & Bear

[57] ABSTRACT

The present invention relates, in general, to a DNA segment. In particular, the present invention relates to a DNA segment coding for a polypeptide having an amino acid sequence corresponding to RhoNUC, a polypeptide having an amino acid sequence corresponding to RhoNUC, antibodies to RhoNUC, a recombinant DNA molecule, a cell containing the recombinant DNA molecule, and methods of producing and using the polypeptide and DNA segment.

12 Claims, 5 Drawing Sheets

OTHER PUBLICATIONS

Fraser, M. et al., "An immunochemical study of Neurospora nucleases" *Biochem. Cell Biol.* 64:106–116.

Madaulel, P. and Axel, R., "*A novel ras-Related Gene Family,*" *Cell.* 41:31–40 (1985).

Devereux, J. et al., "A comprehensive st of sequence analysis programs for the V A X," *Nucleic Acids Research* 12:387–395 (1984).

Resnick, M. et al., "DNA Polymerases, Deoxyribonucleases, and recombination during meiosis in *Saccharaomes cerevisiae*" *Mol. Cell Biol.* 4:2811–2817 (1984).

Chaudhury A. and Smith G., "A new class of *Escherichia coli* recBC mutants: Implications for the role of RecBC enzyme in homologous recombination," *Proc. Natl. Acad. Sci. USA* 81:7850–7854 (1984).

Rothestein, R., "One-step gene disruption in yeast" *Methods in Enzymology* 101:202–221 (1983).

Chow, T. and Fraser, M., "Purification and properties of single strand DNA-binding endo-exonuclease of *Neurospora crassa*" *J. Biol. Chem.* 258:12010–12018 (1983).

Elder, T. et al., "RNA from the yeast transposable element tyl has both ends in the direct repeats a structure similar to retrovirus RNA" *Proc. Natl. Acad. Sci. USA* 80:2432–2436 (1983).

Young, A. and Davis, R., "Efficient isolation of genes by using antibody probes" *Proc. Natl. Acad. Sci. USA* 80:1194–1198 (1983).

Malone, R. and Esposito, R., "The RAD52 gene is required for homothallic interconversion of mating types and spontaneous mitotic recombination in yeast," *Proc. Natl. Acad. Sci.* 77:503–507 (1980).

Towbin, H. et al., "Electrophoretic transfer of proteins from polyacrylamide gels to mitrocellulose sheets: Procedure and some applications," *Proc. Natl. Acad. Sci. USA* 76:4350–4354 (1979).

Chow, T. and Fraser, M., "The major intracellular alkali deoxyribonuclease activities expressed in wild-type and Rec-like mutants of *Neurospora crassa*" *Can. J. Biochem.* 57:889–901 (1979).

Sanger F. and Coulson, A., "The use of thin acrylamide gels for DNA sequencing" *MRS Lab. Mol. Biol.* 87:107–110 (1978).

McMaster G. and Charmichael, G., "Analysis of single- and double-stranded nucleic acids on polyacrylamide and agarose gels by using glyoxal and acridine orange" *Proc. Natl. Acad. Sci. USA* 74:4835–4838 (1977).

Berk, A. and Phillip, A., "Sizing and mapping of early adenovirus mRNAs by gel electrophoresis of S1 endonuclease-digested hybrids" *Cell.* 12:721–731 (1977).

Resnick, M. and Martin, P., "The repair of double-strand breaks in the Nuclear DNA of *Saccharomyces cerevisiae* and its genetic control" *Molec. gen. Genet.* 143:119–129 (1976).

Kohler, G. and Milstein C., "Continuous cultures of fused cells secreting antibody of predefined specifity" *Nature* 256:495–497 (1975).

Zhu, H. et al., "Determination of the carboxyl termini of the alpha and beta subunits of yeast K1 killer toxin" *J. Biol. Chem.* 262:10728–10732 (1987).

Ho, K. and Mortimer, R., "Induction of dominant lethality by x-rays in a radiosensitive strain of yeast," *Mutation Research* 20:45–51 (1973).

Hollowman, W. and Holliday, R., "Studies on a nuclease from *Ustilago maydis*" *J. Biol. Chem.* 23:8107–8113 (1973).

Fraser, M. et al., "Nucleases and their control in wild-type and nuh mutants for neurospora" *Dept. Biochem. Biol. McGill University* Chapter 5:63–74 (1979).

Young, R. and Davis, R., "Yeast RNA polymerase II genes; Isolation with antibody probes," *Science* 222:778–782 (1983).

Chow, T. et al., "Repair and recombination defective mei-41 mutants of drosophila lack a Dnase which is related to nucleases from fungi" *J. Cell. Biochem.* 10B:211 (1986), Abst. No. 1245.

Fig. 3

```
YNUCR   51  SLSTIPSYEQ MKRTNKLPDY HLKIVVVGDG AVGKTCLLIS YVQGTFPTDY
             ..  ..     ........  . .......  .  .......  .........
HUMRHO   1                   MAAI RKKLVVVGDG ACGKTCLLIV FSKDEFPEVY

YNUCR  101  IPTIFENYVT NIEGPNGQII ELALWDTAGQ EEYSRLRPLS YTNADVLMVC
             .. ......  ..  .      ..........  ..  .....  .  ..... .
HUMRHO  35  VPTVFENYVA DIE-VDGKQV ELALWDTAGQ EDYDRLRPLS YPDTDVILMC

YNUCR  151  YSVGSKTSLK NVEDLWFPEV KHFCPSTPIM LVGLKSDLYE ADNLSDLVEQ
             .. ....  .  .. .  ...  ...  . ..  ..  ....   .  ..  .
HUMRHO  85  FSVDSPDSLE NIPEKWVPEV KHFCPNVPII LVANKKDLRS DEHVRTELAR

YNUCR  201  VQQNPWPSVW GHLHIFKCSA RLKENIDEVF ETAIHTLLSD SLYAPREPTH
             ..
HUMRHO 135  MKQEPVRTDD GRAMAVRIQA YDYLECSAKT KEGVREVFET ATRAALQKRY

YNUCR  251  TIKNPFKRNT TSQYRFFYWR YQRLYFRNEK IKKKQVYYNV RIMMKIILLP

HUMRHO 185  GSQNGCINCC KVLX
```

```
-119  TG ATT AAG TAG TTA TAG CCT TAC GTT AAG ACG ACA AAA GAC CAT GAT AAG CAT CCC TCA AAA  -58
-57   GTT ACA GCA AAC TTA AGT CAA ATA GGT CAC AAA AAT CTC CAA TAG TAA CGC TTT TTC ATG      3
                                                                                    M
4     AAT ACA CTA TTA TTT AAG CGA AAA GGT GGC AAT TGT GGG AAC GAA AGT AAC ATA GTT TCG    63
      N   T   L   L   F   K   R   K   G   G   N   C   G   N   E   S   N   I   V   S
64    CAG GGA TCG CCC TCA AGT AGC AAT CTT CCT GAA TCA CCT GGC ACT TTA GAT GAA AAG AAT   123
      Q   G   S   P   S   S   S   N   L   P   E   S   P   G   T   L   D   E   K   N
124   CTC CAG ATT GCC TAC TCA TTC GCT AGA AGC CTT TCT ACC ATT CCT AGT TAT GAG CAG ATG   183
      L   Q   I   A   Y   S   F   A   R   S   L   S   T   I   P   S   Y   E   Q   M
184   AAA CGT ACA AAC AAA CTG CCA GAT TAT CAC CTA AAG ATT GTT GTT GTG GGA GAT GGC GCT   243
      K   R   T   N   K   L   P   D   Y   H   L   K   I   V   V   V   G   D   G   A
244   GTA GGG AAG ACG TGC CTG CTG ATA TCT TAT GTC CAA GGA ACA TTT CCG ACT GAT TAT ATT   303
      V   G   K   T   C   L   L   I   S   Y   V   Q   G   T   F   P   T   D   Y   I
304   CCT ACT ATT TTC GAA AAT TAT GTC ACA AAC ATA GAA GGA CCC AAC GGT CAA ATT ATA GAA   363
      P   T   I   F   E   N   Y   V   T   N   I   E   G   P   N   G   Q   I   I   E
364   TTG GCA TTA TGG GAC ACT GCC GGC CAA GAA GAG TAT AGT AGA CTT AGA CCG CTT TCA TAT   423
      L   A   L   W   D   T   A   G   Q   E   E   Y   S   R   L   R   P   L   S   Y
424   AGG AAT GCA GAT GTG CTG ATG GTG TGC TAT TCT GTT GGT AGT AAG ACA TCG CTT AAA AAT   483
      R   N   A   D   V   L   M   V   C   Y   S   V   G   S   K   T   S   L   K   N
484   GTG GAA GAT CTC TGG TTC CCA GAG GTT AAG CAT TTT TGT CCT TCC ACT CCA ATC ATG CTA   543
      V   E   D   L   W   F   P   E   V   K   H   F   C   P   S   T   P   I   M   L
544   GTC GGC CTT AAA TCA GAT CTA TAT GAA GCT GAT AAC CTT TCA GAT CTG GTG GAA CAA GTT   603
      V   G   L   K   S   D   L   Y   E   A   D   N   L   S   D   L   V   E   Q   V
604   CAG CAG AAT CCT TGG CCA AGC GTC TGG GGg CAT TTG CAC ATA TTC AAG TGC TCA GCA CGA   663
      Q   Q   N   P   W   P   S   V   W   G   H   L   H   I   F   K   C   S   A   R
664   TTG AAA GAA AAT ATC GAT GAA GTA TTT GAA ACT GCC ATA CAC ACG TTA CTT TCC GAT TCA   723
      L   K   E   N   I   D   E   V   F   E   T   A   I   H   T   L   L   S   D   S
724   TTA TAT GCT CCC AGA GAG CCT ACA CAT ACA ATC AAA AAT CCC TTT AAA AGA AAT ACC ACC   783
      L   Y   A   P   R   E   P   T   H   T   I   K   N   P   F   K   R   N   T   T
784   AGT CAG TAT CGA TTC TTC TAC TGG AGA TAC CAG CGT CTC TAT TTC CGG AAC GAA AAG ATT   843
      S   Q   Y   R   F   F   Y   W   R   Y   Q   R   L   Y   F   R   N   E   K   I
844   AAG AAA AAA CAA GTG TAT TAT AAT GTA AGA ATA ATG ATG AAG ATT ATT CTG TTG CCC ATT   903
      K   K   K   Q   V   Y   Y   N   V   R   I   M   M   K   I   I   L   L   P   I
904   CTG TAC GcA CTT ACA ACA TTT Gaa aaG TGG CAA GAA AAA ATA CAC ACA TTT TAC GAA CAG   963
      L   Y   A   L   T   T   F   E   K   W   Q   E   K   I   H   T   F   Y   E   Q
964   TTT GAA TTT TCT TTT TTT TTC TTC GAA AAT TCA GAC AAT AAG GTT AAA TAT AAA GCT TAT  1023
      F   E   F   S   F   F   F   F   E   N   S   D   N   K   V   K   Y   K   A   Y
1024  CTC ATC TCA TCG ATA AAA CGC TGG AGT ATT ATC ACA TGC ATG CGT TGC TTT TGG ACC GTA  1083
      L   I   S   S   I   K   R   W   S   I   I   T   C   M   R   C   F   W   T   V
1084  CAG AAG TCT ATA TTT AAA GCT AGG TTT TTC GCT TGC AGA AAC TTT GTC AAG AAG CAT AAT  1143
      Q   K   S   I   F   K   A   R   F   F   A   C   R   N   F   V   K   K   H   N
1144  TAT AAA CTA ATC AGC ACC ATG ACT GGA AGT ACT GAA ATG GTA CCA CCA ACA ATG AAA CAT  1203
      Y   K   L   I   S   T   M   T   G   S   T   E   M   V   P   P   T   M   K   H
1204  ACC GTT GAC AAC AAA AGG CTT TCG TCA CCT TTG ACA GAT TCT GGT AAC CGC CGG ACT AAG  1263
      T   V   D   N   K   R   L   S   S   P   L   T   D   S   G   N   R   R   T   K
1264  AAG CCA AAG TTG AGA AAG TAC AAG GCC AAA AAG GTT GAA ACA ACT TCT CCG ATG GGT GTC  1323
      K   P   K   L   R   K   Y   K   A   K   K   V   E   T   T   S   P   M   G   V
1324  CTA GAA TTT GAA GTG AAC GAT TTG TTA AAA TCT CAA AAT TTG TCC AGG GAG CAG GTT CTG  1383
      L   E   F   E   V   N   D   L   L   K   S   Q   N   L   S   R   E   Q   V   L
1384  AAC GAT GTT ACT TCA ATT CTA AAT GAT AAG TCC TCA ACA GAT GGA CCT ATC GTC TTA CAA  1443
      N   D   V   T   S   I   L   N   D   K   S   S   T   D   G   P   I   V   L   Q
1444  TAT CAC CGA GAG TAA AAA ATG TCA AGG TCT TAG AAA TTA CTT CCA ATG GCA ACG GGT TGG  1503
      Y   H   R   E   -
1504  CTT TGA TCG ATA ATC CTG TTG AAA CAG AAA AGA AGC AAG TTG TTA TCA TAC CGT TTG GCC  1563
1564  TGC CCG GTG ATG TAG TTA ATA TCA AAG TCT TTA AGA CCC ACC CTT ACT ATG TCG AGA GTG  1623
1624  ATT TAT TAG ACG TAG TGG AAA AAT CTC CAA TGA GAA GAG ATG ATT TAA TTA GGG ATA AAT  1683
1684  ATT TCG GGA AAT CTT CAG GAA GTC AAT TAG AGT TCT TAA CTT ACG ATG ACC AAC TAG AAT  1743
1744  TGA AAA GAA AAA CAA TTA TGA ATG CCT ACA AGT TCT TCG CAT TAA GGT TAG TTG CTG AAA  1823
1824  AAC TTT TAC CCC CAT TTG ACA CCA CCG TAG CTT CCC CTT TAC AAT TTG GCT ACA GGA CCA  1883
1864  AAA TTA CGC CTC ATT TCG ATA TGC AAA AAA GAA AAC AAA AGG AAC TAT CAG TAA GGC CTC  1923
1924  CTT TAG ATT TGG TCA AAA GGG TAG ACC TCA ATG GAG AAA AGA TAC TTT GGA TAT CGG CGG  1983
1984  ACA TGG TTC GAT ATT AGA TAT CGA TGA ATG TGT GCT TGC AAC TGA AGT TCT CAA CAA AGG  2043
2044  ATT GAC TAA TGA AAG AAG AAA GTT TGA GCA AGA GTT TAA AAA CTA CAA AAA AGG CGC GAC  2103
2104  TAT TTT ACT GAG AGA GAA TAC CAC TAT TTT AGA CCC TTC CAA ACC AAC TTT AGA ACA GTT  2163
```

CHIMERIC PROTEIN THAT HAS A HUMAN RHO MOTIF AND DEOXYRIBONUCLEASE ACTIVITY

This application is a continuation of application Ser. No. 07/674,801, filed Mar. 26, 1991 now abandoned.

BACKGROUND OF THE INVENTION

1. Field of the Invention

The present invention relates, in general, to a DNA segment. In particular, the present invention relates to a DNA segment coding for a polypeptide having an amino acid sequence corresponding to RhoNUC, a polypeptide having an amino acid sequence corresponding to RhoNUC, antibodies to RhoNUC, a recombinant DNA molecule, cells containing RhoNUC, and methods of producing and using the polypspride and DNA segment.

2. Background Information

Repair processes in the yeast Saccharomyces cerevisiae are under extensive genetic control involving over 50 genes; among these are genes that function in recombinational repair as well as normal meiotic and mitotic recombination (Kunz, B.A., and R. H. Haynes (1981) Annu. Rev. Genet. 15:57–89; Game, J.C. (1983) in: Yeast Genetics, Fundamental and Applied Aspects (eds. Spencer, J.F.T., Spencer, D., and Smith, A.) pgs. 109–137, Springer-Verlag New York, Inc., New York, and Resnick, M.A. (1987) in: Meiosis (ed. Moens, P.), pgs. 157–212, Academic Press, New York). Deoxyribonucleases are expected to play a role in many repair processes since they enable the excision of damaged DNA and provide a means for héteroduplex formation and processing in recombination. Several deoxyribonucleases have been shown both genetically and biochemically to function in recombination and repair. For example, the nuclease activity associated with the *Escherichia coli* recBCD proteins is required for much of host recombination and also for chistimulated lambda bacteriophage (Chaudhury, A.M., and G. R. Smith (1984) Proc. Natl. Acad. Sci. (USA) 81:7850–7854). Holloman and Holliday (J. Biol. Chem. 248:8107–8113, 1973) have described nuclease α from the eucaryote *Ustilago maydis* that is required for recombination and DNA repair. Because of the complex genetic control involving two genes, the specific role of this nuclease has not been ascertained. An endo-exonuclease from *Neurospora crassa* has also been implicated in recombination and repair (Chow, T.Y.-K, and M. F. Fraser (1979) Can. J. Biochem. 57:889–901; Chow, T.Y.-K, and M. F. Fraser (1983) J. Biol. Chem. 258:12010–12018, and Ramotar, D., et al. (1987) J. Biol. Chem. 262:425–431). The phenotypes of mutants deficient or altered in nuclease activity include meiotic sterility and sensitivity to ultraviolet light, X-rays, and/or alkylating agents (Fraser, M.J., et al. (1990) in: DNA repair and mutagenesis in Eucaryotes (Generoso et al., eds) pgs. 63–74, Plenum Publishing Corp., New York). A similar endo-exonuclease has also been isolated from Aspergillus nidulans (Koa, H., et al. (1990) Biochem. Cell. Biol. 68:387–392) and from mammalian mitochondria (Tomkinson, et al., (1986) Nucl. Acids Res. 14:9579–9593).

An endo-exonuclease, RhoNUC, from S. cerevisiae was isolated and characterized and was suggested to function in both repair and recombination (Chow, T.Y.-K, M. A. Resnick (1987) J. Biol. Chem. 262:17659–17667, and Chow, T.Y.-K, and M. A. Resnick (1988) Molec. Gen. Genet. 211:41–48; Because of the chimeric nature of the endoexonucleasei this protein is now referred to as RhoNUC, rather than the original yNUCR reported in these papers and the gene encoding RhoNUC is named RNC1 for Rho-associated-Nuclease). Several properties of RhoNUC resemble those of the *E. coli* recBCD nuclease. The RhoNUC activity in both mitotic and meiotic cells is greatly influenced by a functional RAD52 gene. The RAD52 gene product is required for mitotic and meiotic recombination and for the repair of double stranded breaks in DNA. Mutants deficient in the gene product (rad52) cannot proceed properly through meiosis. Meiotic recombination is abolished in rad52 mutants, and cells die as they enter the meiotic cycle. In rad52 mutants, the mitotic level of the endo-exonuclease is less than 10% of the wild type level, and no increase is observed during meiosis (Resnick, M.A. et al. (1984) Molec. Cell. Biol. 4:2811–2817).

SUMMARY OF THE INVENTION

It is a general object of this invention to provide a DNA segment encoding RhoNUC.

It is a specific object of this invention to provide a polypeptide corresponding to RhoNUC.

It is another object of the invention to provide a recombinant DNA molecule comprising a vector and a DNA segment encoding RhoNUC.

It is a further object of the invention to provide a cell that contains the above-described recombinant DNA molecule.

It is another object of the invention to provide a cell containing the RNC1 gene.

It is a further object of the invention to provide antibodies to RhoNuc.

It is another object of the invention to provide a method of controlling cell cycle.

It is yet another object of the invention to provide a method of controlling cell development.

Further objects and advantages of the present invention will be clear from the description that follows.

In one embodiment, the present invention relates to a DNA segment coding for a polypeptide having an amino acid sequence corresponding to RhoNUC wherein said polypeptide has deoxyribonuclease activity and the N-terminal sequence of said polypeptide encodes a human rho/ras onocogene-like motif.

In another embodiment, the present invention relates to a polypeptide free of proteins with which it is naturally associated (or bound to a solid support) and having an amino acid sequence corresponding to RhoNUC wherein said polypeptide has deoxyribonuclease activity and the N-terminal sequence of said polypeptide encodes a human rho/ras onocogene-like motif.

In a further embodiment, the present invention relates to a recombinant DNA molecule comprising a vector and the above-described DNA segment.

In another embodiment, the present invention relates to a cell that contains the above-described recombinant DNA molecule.

In a further embodiment, the present invention relates to a cell containing the RNC1 gene, wherein the RNC1 gene contains a mutation in the region of said gene that encodes an amino acid sequence that confers deoxyribonuclease activity on the protein product encoded in the gene.

In another embodiment, the present invention relates to a cell containing the RNC1 gene, wherein the RNC1 gene contains a mutation in the region of the gene that encodes an amino acid sequence that contains the rho/-ras oncogene-like motif encoded in the gene.

In a further embodiment, the present invention relates to a DNA segment that complements the above-described mutations.

In yet another embodiment, the present invention relates to an antibody having binding affinity to Rho-NUC, or a unique portion thereof.

In another embodiment, the present invention relates to a method of controlling cell cycle comprising introducing into a host cell the above-described DNA segment and effecting expression of the DNA segment under conditions such that the cell cycle is controlled.

In a further embodiment, the present invention relates to a method of controlling cell development comprising introducing into a host cell the above described DNA segment and effecting expression of the DNA segment under conditions such that the cell development is controlled.

BRIEF DESCRIPTION OF THE DRAWINGS

FIG. 1. Restriction endonuclease map of insert from (A) λgt11 clone and from (B) YEp213-10. The location of mini-Tn10 transposon insertion in λgt11 and of LEU2 gens disruption are indicated by the inverted triangle. The open reading frame of the RNC1 gens was indicated by the arrow (a). The restriction endonuclease symbols are: R1, EcoR1; X1, XhoI; Bm1, BamH1; K1, Kpn1; H3, HindIII; Sp1, Sph1; B1, BglII; and S1, Sal1.

FIG. 2. Nucleotide sequence of RNC1 (SEQ ID NO:1) and its corresponding translated amino acid sequence (SEQ ID NO:2). The five amino acids underlined correspond to the five amino acids determined by protein sequence with the purified yeast RhoNUC endo-exonuclease protein.

FIG. 6. Methylmethanesulfonate (MMS)survival of A: RAD+ cells and RAD+[YEp213-10] cells. The heavy lines correspond to stationary cells and the dashed to logarithmically growing cells: (o) no plasmid; (inverted triangle) contains YEP213-10.

DETAILED DESCRIPTION OF THE INVENTION

The present invention relates, in part, to a DNA segment coding for a polypeptide having an amino acid sequence encoding a human rho motif wherein the polypspride has deoxyribonuclease activity and is Rho-NUC. In one embodiment, the DNA segment has the sequence shown in SEQ ID NO:1, or allelic or species variation thereof. In another embodiment, the DNA segment encodes the amino acid sequence set forth in SEQ ID NO:2, or allelic or species variation thereof.

In another embodiment, the present invention relates to a polypeptide free of proteins with which it is naturally associated (or bound to a solid support) and having an amino acid sequence encoding a human rho motif wherein said polypeptide has deoxyribonuclease activity and is RhoNUC. In one preferred embodiment, the polypeptide has the amino acid sequence set forth in SEQ ID NO:2, or allelic or species variation thereof.

In a further embodiment, the present invention relates to a recombinant DNA molecule comprising a vector (for example—a plasmid or viral vector) and the above-described DNA segment. In a preferred embodiment, the encoding segment is present in the vector operably linked to a promoter.

In another embodiment, the present invention relates to a cell containing the above-described recombinant DNA molecule. Suitable host cells include procaryotes (such as bacteria, including E. coli) and both lower eucaryotes (for example—yeast) and higher eucaryotes (for example—mammalian or Drosophila cells). Introduction of the recombinant molecule into the host cell can be effected using methods known in the art.

In a further embodiment, the present invention relates to a cell containing the RNC1 gene, wherein the RNC1 gene contains a mutation in the region of said gene that encodes an amino acid sequence that confers deoxyribonuclease activity on the protein product encoded in the gene.

In another embodiment, the present invention relates to a cell containing the RNC1 gene, wherein the RNC1 gene contains a mutation in the region of the gene that encodes an amino acid sequence that contains the rho/-ras oncogene-like motif encoded in the gene.

In a further embodiment, the present invention relates to a DNA segment that complements the above-described mutations.

In a further embodiment, the present invention relates to an antibody having binding affinity to RhoNUC, or a unique portion thereof. In one preferred embodiment, RhoNUC has the amino acid sequence set forth in SEQ ID NO:2, or allelic or species variation thereof. In another preferred embodiment, the unique portion is selected from the group corresponding to amino acid position 1-395 set forth in SEQ ID NO:2, amino acid position 1-195 set forth in SEQ ID NO:2, amino acid 195-486 set forth in SEQ ID NO:2, or amino acid position 395-486 set forth in SEQ ID NO:2.

Antibodies can be raised to RhoNUC, or unique portions thereof, in its naturally occuring form and in its recombinant form. Additionally, antibodies can be raised to RhoNUC in both its active form and inactive form, the difference being that antibodies to the active RhoNUC are more likely to recognize epitopes which are only present in the active RhoNUC.

RhoNUC may be joined to other materials, particularly polypeptides, as fused or covalently joined polypeptides to be used as immunogens. RhoNUC or its fragments may be fused or covalently linked to a variety of immunogens, such as keyhole limpet hemocyanin, bovine serum albumin, tetanus toxoid, etc. See for example, Microbiology, Hoeber Medical Division (Harper and Row, 1969), Landsteiner, Specificity of Serological Reactions (Dover Publications, New York, 1962) and Williams et al., Methods in Immunology and Immunochemistry, Vol. 1 (Academic Press, New York, 1967), for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts. Description of techniques for preparing such monoclonal antibodies may be found in Stites et al., editors, Basic and Clinical Immunology, (Lange Medical Publications, Los Altos, Calif., Fourth edition) and references cited therein, and in particular in Kohler and Milstein in Nature 256:495–497 (1975), which discusses one method of generating monoclonal antibodies.

In a further embodiment, the present invention relates to a method of producing the above-described polypeptide, comprising culturing the above-described host cells under conditions such that the polypeptide is produced, and isolating the polypeptide.

In another embodiment, the present invention relates to a method of controlling cell cycle comprising introducing into a host cell the above-described DNA segment and effecting expression of the DNA segment under conditions such that the cell cycle is controlled. This can be accomplished by increasing the copy number or expression of the RhoNUC which results in altered cell growth and formation of nucleii. Alternatively, growth could be modified by chemicals that would interfere with either or both the rho-related function or the deoxyribonuclease function.

In a further embodiment, the present invention relates to a method of controlling cell development comprising introducing into a host cell the above-described DNA segment and effecting expression of the DNA segment under conditions such that the cell development is controlled. This would provide for the regulation and/or delay of germinal development either by overexpression or underexpression of the RNC1 gene or modifications of portions of that gene. Alternatively, development may be modified by chemicals that could interfere with either or both the rho related function of the deoxyribonuclease function.

The DNA sequences and polypeptides according to this invention exhibit a number of utilities including but not limited to:

1. Utilizing the RNC1 DNA sequence or the RhoNUC polypeptide to isolated mutants from yeast or other organisms and to study these mutants.

2. Utilizing the RNC1 DNA sequence or the RhoNUC polypeptide to characterize agents and drugs that would modify cellular growth and development.

3. Utilizing the RNC1 DNA sequence or the RhoNUC polypeptide to isolate associated proteins.

4. Utilizing the RhoNUC polypeptide as well as proteins from related mutants to obtain antibodies to the entire RhoNUC protein or various internal epitopes.

The present invention is described in further detail in the following non-limiting examples.

EXAMPLES

The following protocols and experimental details are referenced in the examples that follow:

Strains and media. The strains used in this study are: TC106d with genotype of Matα leu2 ura3 his1 trp1, and TC107a with genotype of Matα leu2 ura3 his1 trp1 rad52. TC80c has a genotype of Matα leu2 ura3 trp1, and TC105d has a genotype of Matα leu2 his1 trp1. These strains were congenic and closely related to the efficient sporulating strain SK1. The diploid strain for gene disruption was TC80c X Tc105d. Media for the growth and sporulation of S. cerevisiae as well as standard genetic techniques have been described elsewhere (Methods in Yeast Genetics (ed. Sherman et al.) Cold Spring Harbor Laboratory Press, 1986).

Antibody identification of RNC1 clone. The E. coli strain Y1090 was infected with a yeast genomic expression library in λgt11 (obtained from M. Synder) according to the method described by Young and Davis (Young R.A., and R. W. Davis (1983) Proc. Natl. Acad. Sci. (USA) 80:1194–1198, and Young R.A., and R. W. Davis (1984) Science 222:778–782) and subsequently plated. After incubation for five hours at 37° C., the plates were overlayed with nitrocellulose filters which were previously soaked with 10 mM IPTG and incubated overnight. The nitrocellulose filters were removed and washed once with Tris-HCl pH 7.5 containing 1 mM EDTA and 150 mMNaCl. The filters were processed by a method similar to that of Towbin et al. (Proc. Natl. Acad. Sci. (USA) 76:4350–4354, 1979). The filters were enclosed in boiling pouches with 10–15 ml of buffer A (10 mM Tris-HCl, pH 8.0, 1 mM EDTA, 150 mM NaCl, 2% skim milk powder) and treated for 3 h with antibody (1:200 dilution serum per blot) with continuous gentle agitation at room temperature (approximately 23° C.). The filters were rinsed for 45 min at room temperature in three changes of buffer A lacking skim milk powder, resealed into boiling pouches with 10–15 ml buffer A, and treated for 1.5 h at room temperature with [$^{125}$I]protein A (approximately 1 mCi/blot). Blots were rinsed at room temperature for 15 min in buffer A without skim milk powder and again for 30 min in buffer A containing 1M NaCl without skim milk powder. Finally the filters were rinsed for 15 min in buffer A without skim milk powder. The filters were dried and exposed at room temperature to Kodak XAR-5 X-ray film in Dupont intensifying screens.

Transposition mutagenesis of gt11-RNC1 with mini Tn10 transposable element. Insertion mutagenesis of the coding sequences on λgt11 clones with a mini-Tn10 "transplason" was carried out according to the method described by Snyder et al. (Proc. Natl. Acad. Sci. (USA) 83:730–734, 1986).

Isolation Of RNC1 from YEp213 yeast genomic library. The DNA insert from λgt11 clone was isolated and utilized as probe in obtaining longer insert from YEp213 yeast genomic library. The DNA insert from lambda gt11 was isolated by digesting the DNA with EcoRI and then gel purified. The 3.5 kb fragment was labelled with [$^{32}$P]-dATP by nick translation system (from BRL). E. coli (HB101) transformants with the YEp213 yeast genomic library were probed with this [$^{32}$P]-labelled DNA fragment. The plasmid was isolated from the positive colonies and mapped with restriction endonuclease. The restriction map of the YEp213 plasmid insert was compared with that of the λgt11 clones to confirm the degree of overlap and the amount of extension at both 3' and 5' ends.

DNA sequencing. The DNA fragment containing the RNC1 gene was sequenced according to the method of Sanger and Coulson ( Sanger, F., and A. R. Coulson (1978) FEBS Lett. 87:107–110) using the T7 sequencing kit from Pharmacia.

Northern hydrization and S1 nuclease protection.

Total RNA was isolated according to the method described by Elder et al. (Proc. Natl. Acad. Sci. (USA) 80:2432–2436, 1983). The RNA was denatured in glyoxyl and dimethylsulfoxide and electrophoresed in a 1% agarose gel under the condition described by McMaster and Carmichael (Proc. Natl. Acad. Sci. (USA) 74:4835–4838, 1977). The RNA was then transferred and hybridized with the [$^{32}$P]-labelled 4 kb fragment insert from YEp213-10 according to methods described by Amersham (Amersham's Hybond nylon and nitrocellulose membranes-membrane transfer and detection methods (1986) Amersham Corporation, Arlington Heights, Ill.). S1 nuclease protection followed the procedures of Berk and Sharp (Cell 12:721–732, 1977). 20 mg of total RNA and 0.5 mg of gel purified fragment of the 4 kb insert were precipitated and resuspended in 30 ml of hybridization buffer (40 mM HEPES (pH 6.4), 1 mM EDTA, 0.4M NaCl, and 80% formamide). The nucleic acids were incubated at 85° C. for 10 minutes and then immediately shifted to a 37° C. incubator for overnight incubation. 300 ml of ice cold S1 digestion buffer (0.28M NaCl, 0.05M sodium acetate (pH 4.5), 4.5 mM ZnSO4, 20 mg/ml ssDNA, 200 units/ml S1 nuclease) containing 100 units of S1 nuclease was added. The S1 nuclease digestion reaction was incubated at 23° C. for 3 hours. After alkaline hydrolysis of RNA, the DNA was precipitated with ethanol, dried, and resuspended in 10 ml of sterile distilled water. The DNA was electrophoresed in a 0.7% agarose gel and protected fragment was determined with the 4 kb insert probe which had been radioactively labelled.

Nuclease assay. Endo-exonuclease activity was measured according to the method previously described by Chow and Resnick (in: Cellular Response to DNA Damage, pgs. 447–455, Alan R. Liss, Inc., New York, 1983.).

Methylmethanesulfonate and radiation sensitivity. MMS medium was prepared according to method described by Malone and Esposito (Proc. Natl. Acad. Sci. (USA) 77:503–507, 1980). Logarithmically growing or stationary phase cells containing either vector or a RNC1 plasmid were plated on YEPD agar plates containing different concentration of MMS. The plates were wrapped with parafilm and incubated at 30° C. for 2–3 days. In experiments designed to measure ionizing radiation sensitivity, stationary cells containing either the vector (YEp213) or a RNC1 plasmid were plated on synthetic medium lacking leucine (to maintain the plasmid). The plates were then irradiated in a Gamma Cell 220 (Atomic Energy of Canada).

Genetic mapping of RNC1. To map RNC1 strains carrying a deletion-insertion of RNC1 (EPY109-1D: MATα ura3-52 leu2Δ1 trp1::hisG his1-1 RNC1::TRP1) were crossed to strains carrying chromosome XI URA1 or MET14 markers. Standard genetic mapping techniques were employed.

Chemicals. Tris[hydroxymethyl]aminomethane was obtained from Sigma. Ethylenedinitrilo-tetraacetic acid (EDTA), hydrogen peroxide (30%), and methanol were from Fisher. $^{125}$I-protein A and Hybond-N membrane were from Amersham. Nitrocellulose filters were from Schleicher and Schuell. Restriction endonucleases and the DNA sequence kit were from Pharmacia Fine Chemical. Yeast extracts and Bacto-peptone were obtained from Difco.

EXAMPLE 1

Identification of the RNC1 Gene

Figure 1A:
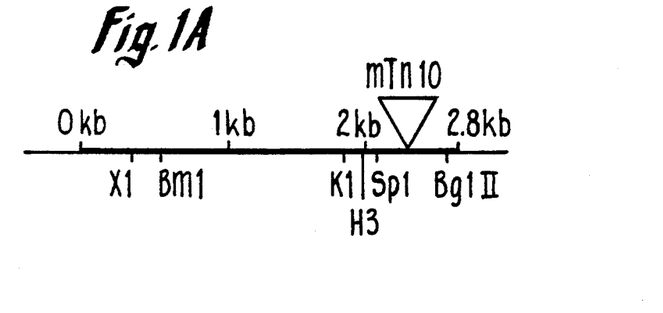
Figure 1B:
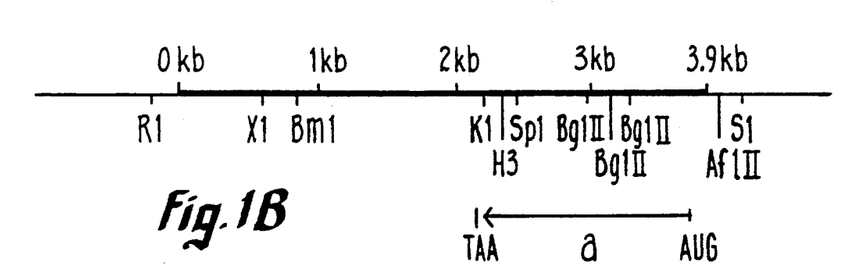

Previously, it was shown that the antibody raised against an endo-exonuclease from N. crassa crossreacts with an endo-exonuclease (RhoNUC) of S. cerevisiae (Chow, T.Y.-K., and M. A. Resnick (1987) J. Biol. Chem. 262:17659–17667, and Chow, T.Y.-K., and M. A. Resnick (1988) Molec. Gen. Genet. 211:41–48). This antibody was used to probe a λgt11 yeast genomic library to isolate the corresponding gene. Among 100,000 phages screened, one clone was obtained that contained a 3 Kb yeast DNA insert (FIG. 1). The crossreacting material in this λgt11 clone can be eliminated by a mini-Tn10 transposable element insertion (Snyder, M. et al. (1986) Proc. Natl. Acad. Sci. (USA 83:730–734) into the DNA segment (data not shown). To ensure the isolation of the complete gene, the 3 kb insert was used to probe a library of larger genomic inserts in YEp213. This led to the isolation of YEp213-10 that contained a 4 kb insert. This plasmid when cut with EcoRI yielded a 3 kb fragment that hybridized with the 3 kb λgt11 fragment; no other fragments exhibited hybridization. The restriction enzyme map of the insert is shown in FIG. 1; regions of overlap between the insert from λgt11 and the insert from YEp213-10 are indicated in FIG. 1.

The DNA sequence of the yeast 4 kb insert in YEp213-10 plasmid contains a 1.4 kb open reading frame (FIG. 2; SEQ ID NO:1 AND SEQ ID NO:2). As shown in FIG. 1, the mini-Tn10 insertion that eliminated cross-reacting material in the λgt11 clone occurred in this region. The sequence is expected to give rise to a protein of 486 amino acids having a molecular weight of 57 kDa (SEQ ID NO:2). The difference between this and the observed 72 kDa could be due to glycosylation at the 4 consensus sequence sites. Phosphorylation seems unlikely since treatment of the purified endo-exonuclease (Chow and Resnick (1987) J. Biol. Chem. 262:17659–17667) with alkaline phosphatase does not change the eletrophoretic mobility in an SDS-polyacrylamide gel (T. Chow, unpublished). The correspondence between RNC1 and the previously isolated RhoNUC was further substantiated from the amino acid sequence of a portion of the purified protein. A five amino acid stretch aspartic-glutamic-lysine-asparagine-leucine was identified that corresponds to the five amino acids located at position 38–42 downstream from the N-terminal methionine (FIG. 2). The lack of identifiable sequence prior to this position is attributed to protein processing.

EXAMPLE 2

Homology of RNC1 with rho/ras genes and E. coli recC

Figure 3:
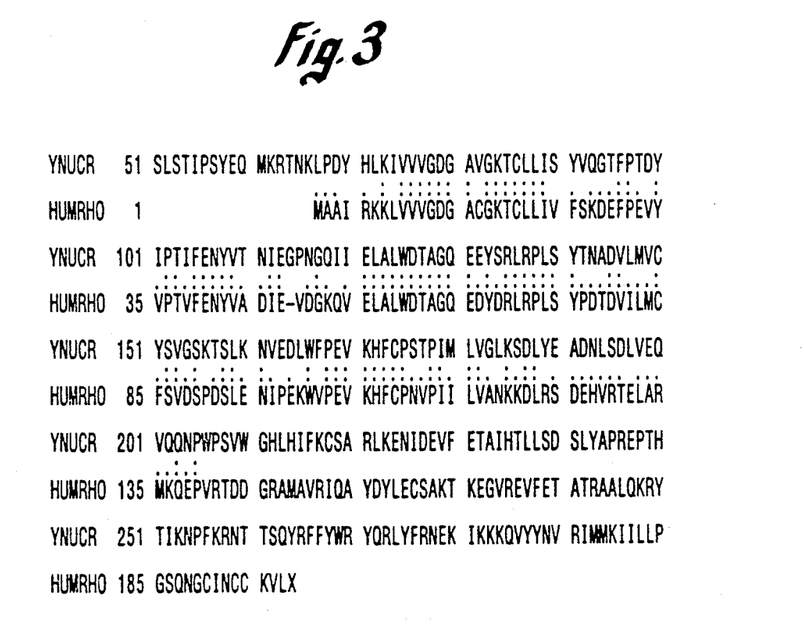
FIG. 3. Comparison of the amino acid sequences encoded by the human rho oncogene with the N-terminal amino acid sequences of RNC1. The alignments were generated by computer as described (Devereux, J., et al. (1984) Nucl. Acids. Res. 12:387-395). The putative GTP binding sites in rho oncogene are underlined.

The N-terminal portion of the RNC1 gene translation product exhibits considerable homolog with mammalian rho genes (FIG. 3). The rho genes are related to ras oncogenes (Chardin et al. (1988) Nucleic Acids Res. 16:2717; Yeramian et al (1987) Nucleic Acids Res. 15:1869; Madaule and Axel (1985) Cell 41:31–40; Madaule et al. (1987) Proc. Nat. Acad. Sci. (USA) 84:779–783). The region between amino acid 67 and 253 has 47% identity and 66% similarity with the human rhoB gene. Comparable homology was found for other rho proteins listed in GENBANK. This region includes the consensus sequence for a GTP binding site. The homology in the C-terminal portion (amino acid 254 to 486) with *E. coli* recC is consistent with previous observations concerning the crossreactivity of the antisera used to isolate the RNC1 gene (16); there is 19% identity and 44% similarity with the recC protein. The translation product appears to be a chimeric protein containing an N-terminal rho-like portion and a C-terminal deoxyribonuclease function. The gene has thus been named RNC1 for Rho associated NuClease (SEQ ID NO:1) and the originally isolated yNucR is identified as RhoNUC protein (SEQ ID NO:2) to emphasize the presence of the highly conserved rho related amino sequence. RNC1 shares no homology with RAD52.

EXAMPLE 3

Expression of RNC1

Figure 4:
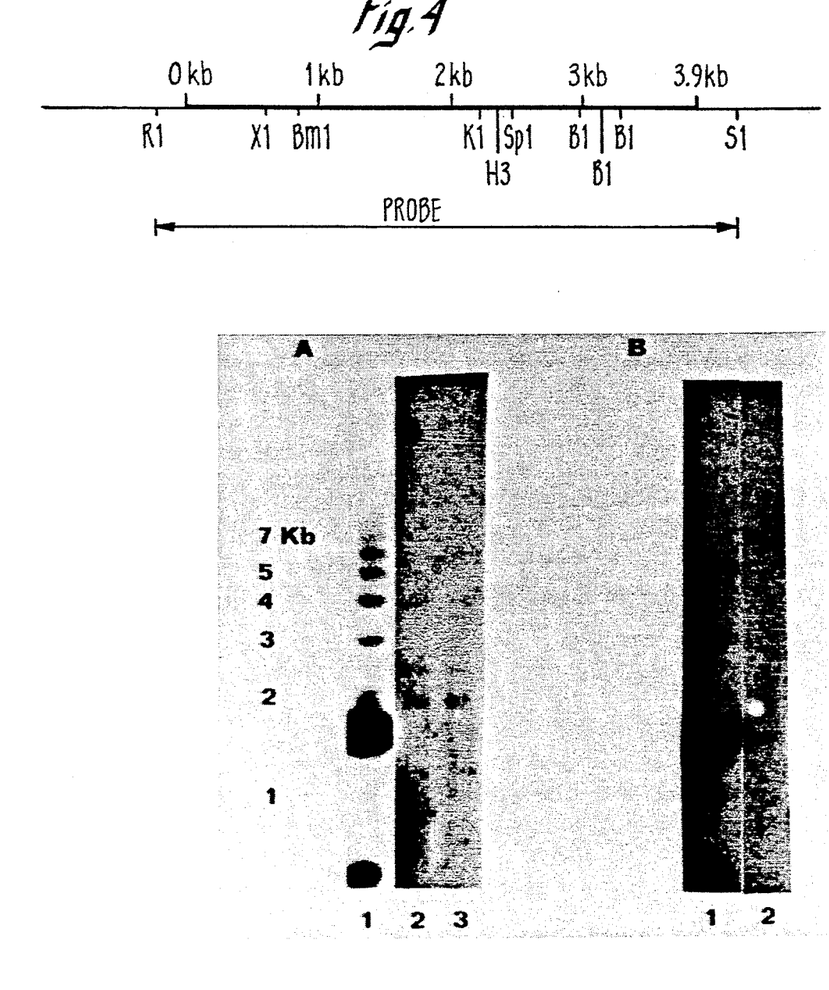
FIG. 4. (A) Northern hybridization of yeast total RNA with the complete insert from YEp213-10 as probe. Lane 1:1 kb molecular weight standard, lane 2: Total RNA from TC106d, lane 3: Total RNA from the diploid TC80c X TC105d. (B) Nuclease S1 protection of the YEp213-10 insert with total yeast mRNA. Lane 1: lkb standard; lane 2: fragment from YEp213-10 protected from nuclease S1. The fragment of YEp213-10 used for hybridization and S1 protection was indicated on the upper panel.

The expression of RNC1 was examined in logarithmically growing RAD+ haploid and diploid cells. Total cellular RNA was isolated, separated by size using gel electrophoresis and subjected to Northern hybridization using the 4 kb yeast insert from YE213-10. A 2.0 kb RNA species was identified (FIG. 4). This RNA provided S1 nuclease protection to a specific 1.5 fragment within the 4 kb insert (FIG. 4).

Figure 5:
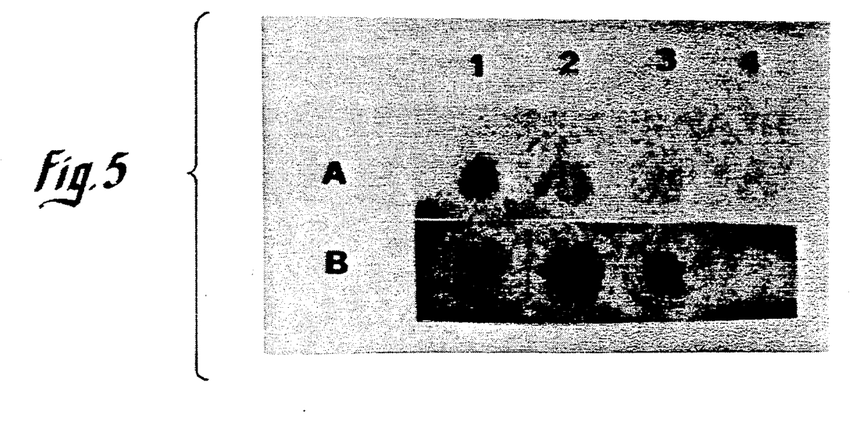
FIG. 5. Antibody cross-reacting material in (A) RAD+ cell extracts and (B) RAD+[YEp213-10] cell extracts. The concentration of protein in each spot are: (1) 112 rag, (2) 56 mg, (3) 28 rag, and (4) 14 mg of protein.

Both RAD+ and rad52 strains were transformed with YEp213-10 and the resulting isolates were examined for antibody crossreacting material in an immuno-dot blot assay and for antibody precipitable DNase activity. The RAD+ yielded more crossreacting reacting material (FIG. 5) and more precipitable activity than the plasmidless controls (1.5 vs 0.8 U/mg protein; Table 1). The low levels of crossreacting material and activity in a rad52 mutant were not enhanced by the presence of the YEP213-10 plasmid (Table 1). The requirement of the RNC1 gene product for growth was also examined. The BglII fragments of RNC1 were removed and replaced by a BamHI-BglII TRP1 containing fragment. The resulting plasmid was cut with Bam HI and AflII and the RNC1-TRP1 containing fragment was used for one-step gene disruption into diploid cells resulting in a deletion/insertion mutation of the gene. The diploids were sporulated and dissected. Since all spores were viable, it was concluded that RNC1 is not essential for growth.

Diploids homozygous for the mutation could exhibit delayed meiotic development by as much as two to three days over the normal single day required for sporulation. This indicates a role for the gene in meiotic development and suggests that mutants may be used to study this developmental process. The mutants may prove useful for isolating genes that complement or suppress this phenotypic defect.

An additional category of mutants has been isolated based on in vitro mutagenesis of the RNC1 gene on a plasmid. When the plasmid was targeted to RNC1 in the cell, mutants were isolated that exhibited temperature sensitivity for growth. This suggests a role for the RNC1 gene in normal cell growth and suggests the possibility of isolating mutants and complementing genes that will suppress the genetic defect. These results are consistent with the observation that overexpression of the RNC1 gene leads to abnormal cell growth and abnormal diffuse nucleii. The amount of RhoNUC may have to be carefully balanced in the cell for appropriate cell growth.

TABLE 1

DEOXYRIBONUCLEASE ACTIVITY IN EXTRACTS OF RAD+, RAD+[YEp213-10], rad52, AND rad52[YEp213-10]

|  | TOTAL DNase (U/mg prot.) | Ab-PRECIPITABLE DNase (U/mg prot.) | % DNase PRECIPITATED |
|---|---|---|---|
| RAD+ | 3.3 | 0.8 | 26 |
| RAD+ [YEp213-10] | 3.4 | 1.5 | 44 |
| rad52 | 3.0 | 0.1 | 3 |
| rad52 [YEp213-10] | 3.1 | 0.3 | 9 |

EXAMPLE 4

Chromosomal localization of RNC1

To identify the physical and genetic location of RNC1, yeast chromosomes were subjected to OFAGE gel electrophoresis and hybridized with the 4 kb insert from YEp213-10. Hybridization was specific to Chromosome XI (data not shown). The genetic location of RNC1 was examined by crossing RNC1::TRP1 mutants with strains containing the centromere marker MET14 and the left arm marker URA1. Meiotic mapping indicates that RNC1 is unlinked to either marker.

EXAMPLE 5

The Phenotype of RAD+ and rad52 Strains Containing Multicopies of RNC1

Figure 6A:
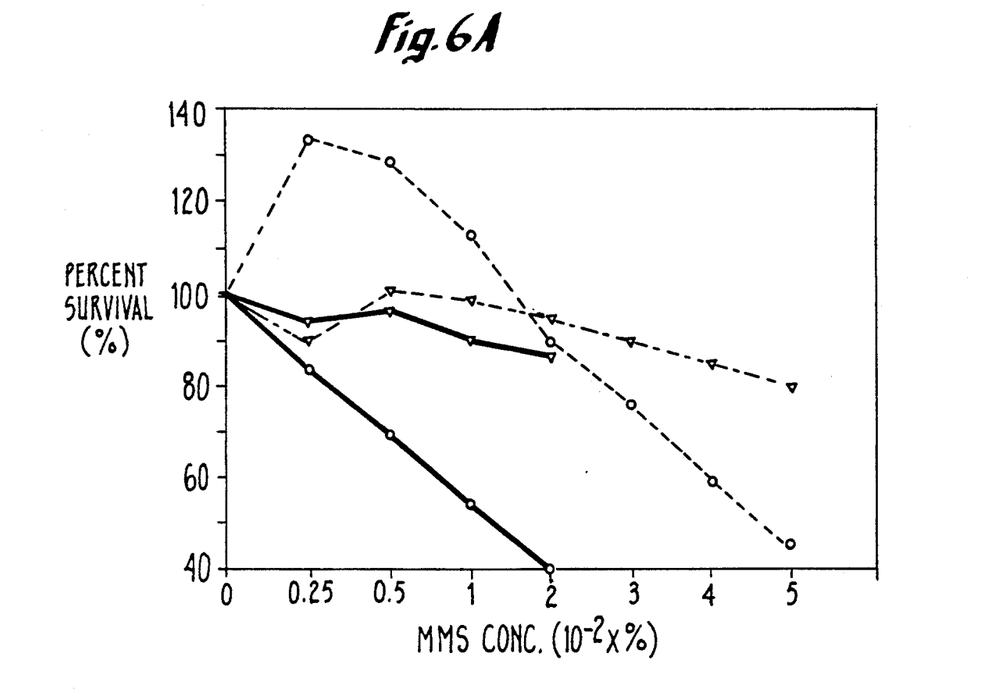
FIG. 6A: RAD+ cells.
Figure 6B:
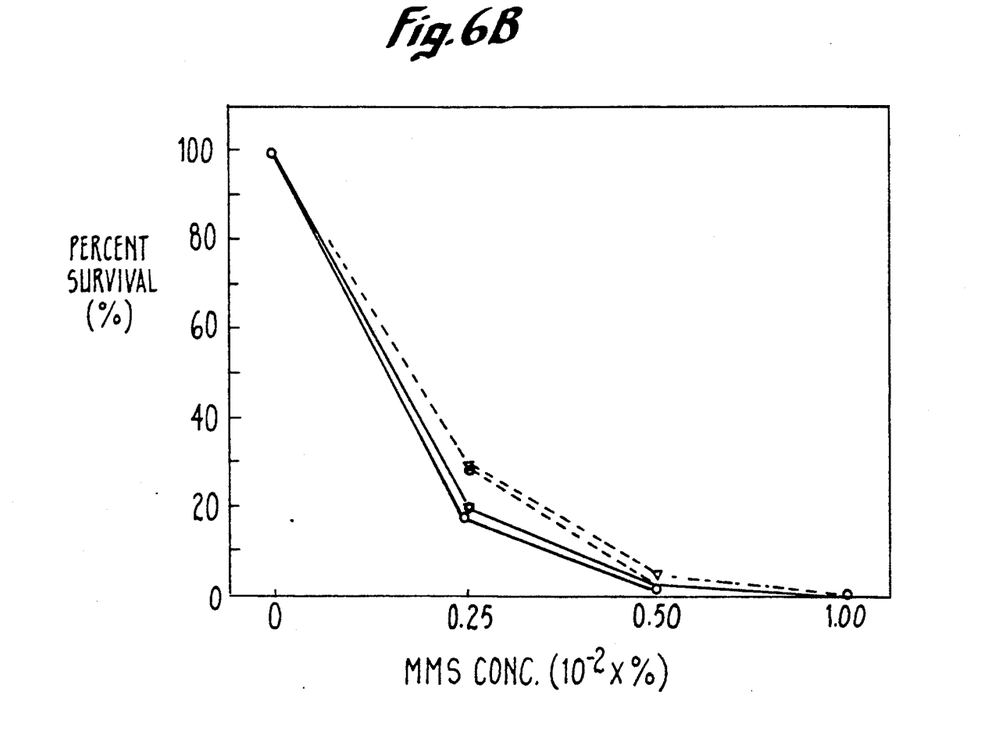
FIG. 6B: rad52 cells.
Figure 7:
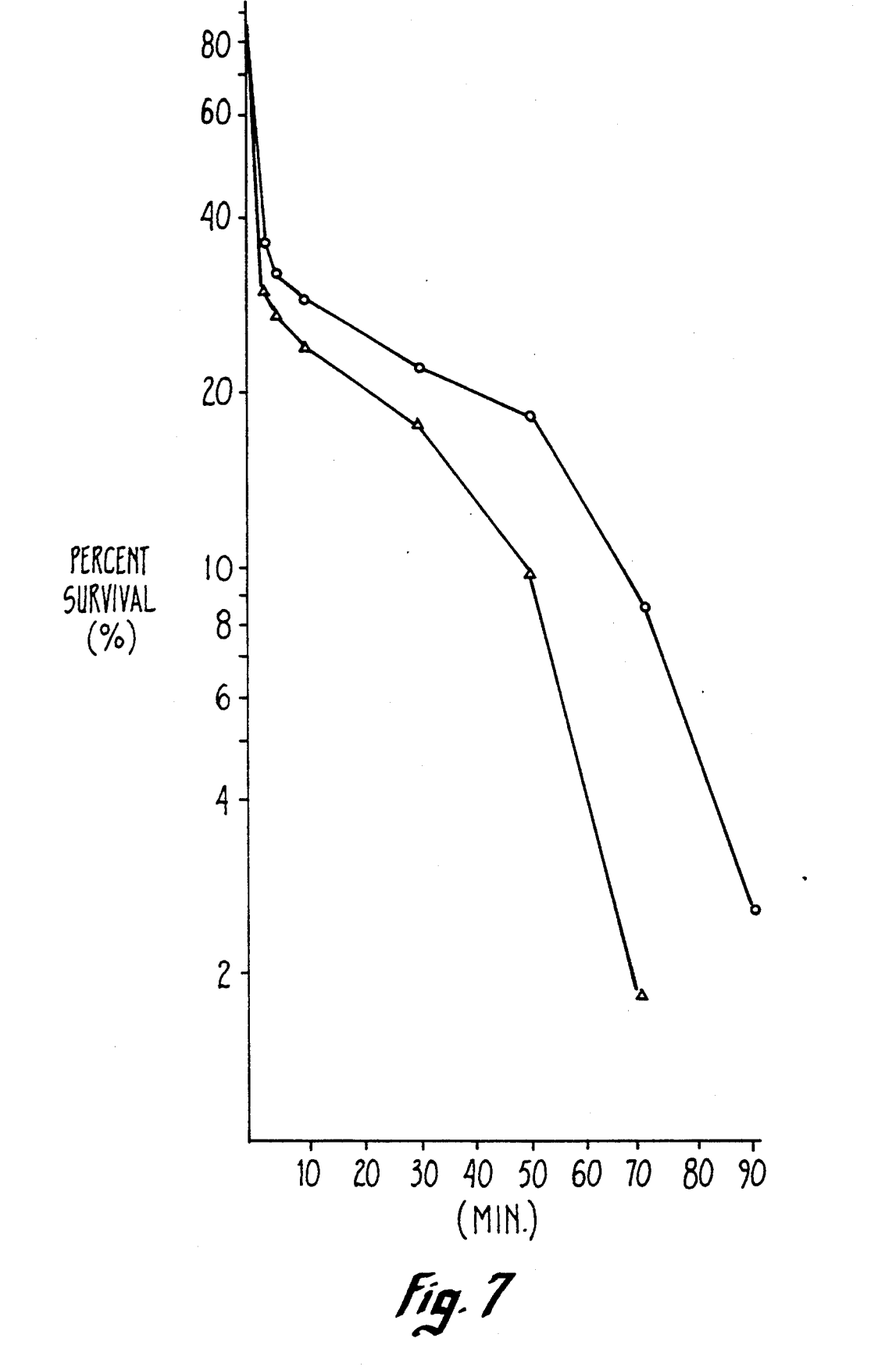
FIG. 7. Cell survival of RAD+[YEp213] (triangles) and RAD+[YEp213-10] (circles) after exposure to ionizing radiation.

To examine the possible function of the RNC1 in DNA repair, RAD+ and rad52 strains containing the high copy YEp213-10 plasmid were exposed to MMS and ionizing radiation. These DNA damaging agents induce lesions that are subject to recombinational repair (Ho, K.S.Y. (1975) Mutat. Res. 20:45-51, and Resnick, M.A., and P. Martin (1976) Mol. Gen. Genet. 13:119-129). Logarithmically growing and stationary haploid cells were plated to YEPD medium containing 0%, 0.0025%, 0.005%, 0.01%, 0.02%, and 0.05% MMS. Stationary RAD+ cells containing YEp213-10 were much more resistant than those lacking the plasmid. The differences in log cells are not as clear, although at higher doses the plasmid-containing cells are more resistant. As shown in FIG. 6, no difference in survival is observed between rad52 cells containing or lacking the YEp213-10 plasmid. Haploid RAD+ cells that contained or lacked the plasmid exhibited similar responses to ionizing radiation (FIG. 7).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2282 base pairs
        ( B ) TYPE: nucleic acid
        ( C ) STRANDEDNESS: double
        ( D ) TOPOLOGY: linear     ( i x ) FEATURE:
        ( A ) NAME/KEY: CDS
        ( B ) LOCATION: 120..1574

( x i ) SEQUENCE DESCRIPTION: SEQ ID NO:1:

```
TGATTAAGTA GTTATAGCCT TACGTTAAGA CGACAAAAGA CCATGATAAG CATCCCTCAA      60

AAGTTACAGC AAACTTAAGT CAAATAGGTC ACAAAATCT  CCAATAGTAA CGCTTTTTC      119

ATG AAT ACA CTA TTA TTT AAG CGA AAA GGT GGC AAT TGT GGG AAC GAA      167
Met Asn Thr Leu Leu Phe Lys Arg Lys Gly Gly Asn Cys Gly Asn Glu
 1               5                  10                  15

AGT AAC ATA GTT TCG CAG GGA TCG CCC TCA AGT AGC AAT CTT CCT GAA      215
Ser Asn Ile Val Ser Gln Gly Ser Pro Ser Ser Ser Asn Leu Pro Glu
             20                  25                  30

TCA CCT GGC ACT TTA GAT GAA AAG AAT CTC CAG ATT GCC TAC TCA TTC      263
Ser Pro Gly Thr Leu Asp Glu Lys Asn Leu Gln Ile Ala Tyr Ser Phe
         35                  40                  45

GCT AGA AGC CTT TCT ACC ATT CCT AGT TAT GAG CAG ATG AAA CGT ACA      311
Ala Arg Ser Leu Ser Thr Ile Pro Ser Tyr Glu Gln Met Lys Arg Thr
     50                  55                  60

AAC AAA CTG CCA GAT TAT CAC CTA AAG ATT GTT GTT GTG GGA GAT GGC      359
Asn Lys Leu Pro Asp Tyr His Leu Lys Ile Val Val Val Gly Asp Gly
 65                  70                  75                  80

GCT GTA GGG AAG ACG TGC CTG CTG ATA TCT TAT GTC CAA GGA ACA TTT      407
Ala Val Gly Lys Thr Cys Leu Leu Ile Ser Tyr Val Gln Gly Thr Phe
                 85                  90                  95

CCG ACT GAT TAT ATT CCT ACT ATT TTC GAA AAT TAT GTC ACA AAC ATA      455
Pro Thr Asp Tyr Ile Pro Thr Ile Phe Glu Asn Tyr Val Thr Asn Ile
            100                 105                 110

GAA GGA CCC AAC GGT CAA ATT ATA GAA TTG GCA TTA TGG GAC ACT GCC      503
Glu Gly Pro Asn Gly Gln Ile Ile Glu Leu Ala Leu Trp Asp Thr Ala
        115                 120                 125

GGC CAA GAA GAG TAT AGT AGA CTT AGA CCG CTT TCA TAT AGG AAT GCA      551
Gly Gln Glu Glu Tyr Ser Arg Leu Arg Pro Leu Ser Tyr Arg Asn Ala
    130                 135                 140

GAT GTG CTG ATG GTG TGC TAT TCT GTT GGT AGT AAG ACA TCG CTT AAA      599
Asp Val Leu Met Val Cys Tyr Ser Val Gly Ser Lys Thr Ser Leu Lys
145                 150                 155                 160

AAT GTG GAA GAT CTC TGG TTC CCA GAG GTT AAG CAT TTT TGT CCT TCC      647
Asn Val Glu Asp Leu Trp Phe Pro Glu Val Lys His Phe Cys Pro Ser
                    165                 170                 175

ACT CCA ATC ATG CTA GTC GGC CTT AAA TCA GAT CTA TAT GAA GCT GAT      695
Thr Pro Ile Met Leu Val Gly Leu Lys Ser Asp Leu Tyr Glu Ala Asp
                180                 185                 190

AAC CTT TCA GAT CTG GTG GAA CAA GTT CAG CAG AAT CCT TGG CCA AGC      743
Asn Leu Ser Asp Leu Val Glu Gln Val Gln Gln Asn Pro Trp Pro Ser
            195                 200                 205

GTC TGG GGG CAT TTG CAC ATA TTC AAG TGC TCA GCA CGA TTG AAA GAA      791
Val Trp Gly His Leu His Ile Phe Lys Cys Ser Ala Arg Leu Lys Glu
        210                 215                 220

AAT ATC GAT GAA GTA TTT GAA ACT GCC ATA CAC ACG TTA CTT TCC GAT      839
Asn Ile Asp Glu Val Phe Glu Thr Ala Ile His Thr Leu Leu Ser Asp
225                 230                 235                 240

TCA TTA TAT GCT CCC AGA GAG CCT ACA CAT ACA ATC AAA AAT CCC TTT      887
Ser Leu Tyr Ala Pro Arg Glu Pro Thr His Thr Ile Lys Asn Pro Phe
                245                 250                 255
```

-continued

| | | | | | | | | | | | | | | | | |
|---|---|---|---|---|---|---|---|---|---|---|---|---|---|---|---|---|
| AAA | AGA | AAT | ACC | ACC | AGT | CAG | TAT | CGA | TTC | TTC | TAC | TGG | AGA | TAC | CAG | 935 |
| Lys | Arg | Asn | Thr | Thr | Ser | Gln | Tyr | Arg | Phe | Phe | Tyr | Trp | Arg | Tyr | Gln | |
| | | | 260 | | | | 265 | | | | | | 270 | | | |
| CGT | CTC | TAT | TTC | CGG | AAC | GAA | AAG | ATT | AAG | AAA | AAA | CAA | GTG | TAT | TAT | 983 |
| Arg | Leu | Tyr | Phe | Arg | Asn | Glu | Lys | Ile | Lys | Lys | Lys | Gln | Val | Tyr | Tyr | |
| | | 275 | | | | | 280 | | | | | 285 | | | | |
| AAT | GTA | AGA | ATA | ATG | ATG | AAG | ATT | ATT | CTG | TTG | CCC | ATT | CTG | TAC | GCA | 1031 |
| Asn | Val | Arg | Ile | Met | Met | Lys | Ile | Ile | Leu | Leu | Pro | Ile | Leu | Tyr | Ala | |
| | 290 | | | | 295 | | | | | | 300 | | | | | |
| CTT | ACA | ACA | TTT | GAA | AAG | TGG | CAA | GAA | AAA | ATA | CAC | ACA | TTT | TAC | GAA | 1079 |
| Leu | Thr | Thr | Phe | Glu | Lys | Trp | Gln | Glu | Lys | Ile | His | Thr | Phe | Tyr | Glu | |
| 305 | | | | | 310 | | | | | 315 | | | | | 320 | |
| CAG | TTT | GAA | TTT | TCT | TTT | TTT | TTC | TTC | GAA | AAT | TCA | GAC | AAT | AAG | GTT | 1127 |
| Gln | Phe | Glu | Phe | Ser | Phe | Phe | Phe | Phe | Glu | Asn | Ser | Asp | Asn | Lys | Val | |
| | | | | 325 | | | | | 330 | | | | | 335 | | |
| AAA | TAT | AAA | GCT | TAT | CTC | ATC | TCA | TCG | ATA | AAA | CGC | TGG | AGT | ATT | ATC | 1175 |
| Lys | Tyr | Lys | Ala | Tyr | Leu | Ile | Ser | Ser | Ile | Lys | Arg | Trp | Ser | Ile | Ile | |
| | | | 340 | | | | 345 | | | | | 350 | | | | |
| ACA | TGC | ATG | CGT | TGC | TTT | TGG | ACC | GTA | CAG | AAG | TCT | ATA | TTT | AAA | GCT | 1223 |
| Thr | Cys | Met | Arg | Cys | Phe | Trp | Thr | Val | Gln | Lys | Ser | Ile | Phe | Lys | Ala | |
| | | 355 | | | | | 360 | | | | | 365 | | | | |
| AGG | TTT | TTC | GCT | TGC | AGA | AAC | TTT | GTC | AAG | AAG | CAT | AAT | TAT | AAA | CTA | 1271 |
| Arg | Phe | Phe | Ala | Cys | Arg | Asn | Phe | Val | Lys | Lys | His | Asn | Tyr | Lys | Leu | |
| | 370 | | | | | 375 | | | | | 380 | | | | | |
| ATC | AGC | ACC | ATG | ACT | GGA | AGT | ACT | GAA | ATG | GTA | CCA | CCA | ACA | ATG | AAA | 1319 |
| Ile | Ser | Thr | Met | Thr | Gly | Ser | Thr | Glu | Met | Val | Pro | Pro | Thr | Met | Lys | |
| 385 | | | | | 390 | | | | | 395 | | | | | 400 | |
| CAT | ACC | GTT | GAC | AAC | AAA | AGG | CTT | TCG | TCA | CCT | TTG | ACA | GAT | TCT | GGT | 1367 |
| His | Thr | Val | Asp | Asn | Lys | Arg | Leu | Ser | Ser | Pro | Leu | Thr | Asp | Ser | Gly | |
| | | | | 405 | | | | 410 | | | | | 415 | | | |
| AAC | CGC | CGG | ACT | AAG | AAG | CCA | AAG | TTG | AGA | AAG | TAC | AAG | GCC | AAA | AAG | 1415 |
| Asn | Arg | Arg | Thr | Lys | Lys | Pro | Lys | Leu | Arg | Lys | Tyr | Lys | Ala | Lys | Lys | |
| | | | 420 | | | | 425 | | | | | 430 | | | | |
| GTT | GAA | ACA | ACT | TCT | CCG | ATG | GGT | GTC | CTA | GAA | TTT | GAA | GTG | AAC | GAT | 1463 |
| Val | Glu | Thr | Thr | Ser | Pro | Met | Gly | Val | Leu | Glu | Phe | Glu | Val | Asn | Asp | |
| | | 435 | | | | | 440 | | | | | 445 | | | | |
| TTG | TTA | AAA | TCT | CAA | AAT | TTG | TCC | AGG | GAG | CAG | GTT | CTG | AAC | GAT | GTT | 1511 |
| Leu | Leu | Lys | Ser | Gln | Asn | Leu | Ser | Arg | Glu | Gln | Val | Leu | Asn | Asp | Val | |
| | 450 | | | | | 455 | | | | | 460 | | | | | |
| ACT | TCA | ATT | CTA | AAT | GAT | AAG | TCC | TCA | ACA | GAT | GGA | CCT | ATC | GTC | TTA | 1559 |
| Thr | Ser | Ile | Leu | Asn | Asp | Lys | Ser | Ser | Thr | Asp | Gly | Pro | Ile | Val | Leu | |
| 465 | | | | | 470 | | | | | 475 | | | | | 480 | |
| CAA | TAT | CAC | CGA | GAG | TAAAAAATGT | CAAGGTCTTA | GAAATTACTT | CCAATGGCAA | 1614 |
| Gln | Tyr | His | Arg | Glu | | | | | |
| | | | | 485 | | | | | |

CGGGTTGGCT TTGATCGATA ATCCTGTTGA AACAGAAAAG AAGCAAGTTG TTATCATACC 1674

GTTTGGCCTG CCCGGTGATG TAGTTAATAT CAAAGTCTTT AAGACCCACC CTTACTATGT 1734

CGAGAGTGAT TTATTAGACG TAGTGGAAAA ATCTCCAATG GAAGAGATG ATTTAATTAG 1794

GGATAAATAT TTCGGGAAAT CTTCAGGAAG TCAATTAGAG TTCTTAACTT ACGATGACCA 1854

ACTAGAATTG AAAAGAAAAA CAATTATGAA TGCCTACAAG TTCTTCGCAT TAAGGTTAGT 1914

TGCTGAAAAA CTTTTACCCC CATTTGACAC CACCGTAGCT TCCCCTTTAC AATTTGGCTA 1974

CAGGACCAAA ATTACGCCTC ATTTCGATAT GCCAAAAAGA AAACAAAGG AACTATCAGT 2034

AAGGCCTCCT TTAGATTTGG TCAAAAGGGT AGACCTCAAT GGAGAAAAGA TACTTTGGAT 2094

ATCGGCGGAC ATGGTTCGAT ATTAGATATC GATGAATGTG TGCTTGCAAC TGAAGTTCTC 2154

AACAAAGGAT TGACTAATGA AAGAAGAAAG TTTGAGCAAG AGTTTAAAAA CTACAAAAAA 2214

GGCGCGACTA TTTTACTGAG AGAGAATACC ACTATTTTAG ACCCTTCCAA ACCAACTTTA 2274

GAACAGTT 2282

(2) INFORMATION FOR SEQ ID NO:2:

(i) SEQUENCE CHARACTERISTICS:
        (A) LENGTH: 485 amino acids
        (B) TYPE: amino acid
        (D) TOPOLOGY: linear     (ii) MOLECULE TYPE: protein     (xi) SEQUENCE DESCRIPTION: SEQ ID NO:2:

```
Met Asn Thr Leu Leu Phe Lys Arg Lys Gly Gly Asn Cys Gly Asn Glu
 1               5                  10                  15

Ser Asn Ile Val Ser Gln Gly Ser Pro Ser Ser Ser Asn Leu Pro Glu
            20                  25                  30

Ser Pro Gly Thr Leu Asp Glu Lys Asn Leu Gln Ile Ala Tyr Ser Phe
            35                  40                  45

Ala Arg Ser Leu Ser Thr Ile Pro Ser Tyr Glu Gln Met Lys Arg Thr
        50                  55                  60

Asn Lys Leu Pro Asp Tyr His Leu Lys Ile Val Val Gly Asp Gly
65                  70                  75                  80

Ala Val Gly Lys Thr Cys Leu Leu Ile Ser Tyr Val Gln Gly Thr Phe
            85                  90                  95

Pro Thr Asp Tyr Ile Pro Thr Ile Phe Glu Asn Tyr Val Thr Asn Ile
            100                 105                 110

Glu Gly Pro Asn Gly Gln Ile Ile Glu Leu Ala Leu Trp Asp Thr Ala
            115                 120                 125

Gly Gln Glu Glu Tyr Ser Arg Leu Arg Pro Leu Ser Tyr Arg Asn Ala
        130                 135                 140

Asp Val Leu Met Val Cys Tyr Ser Val Gly Ser Lys Thr Ser Leu Lys
145                 150                 155                 160

Asn Val Glu Asp Leu Trp Phe Pro Glu Val Lys His Phe Cys Pro Ser
            165                 170                 175

Thr Pro Ile Met Leu Val Gly Leu Lys Ser Asp Leu Tyr Glu Ala Asp
            180                 185                 190

Asn Leu Ser Asp Leu Val Glu Gln Val Gln Gln Asn Pro Trp Pro Ser
        195                 200                 205

Val Trp Gly His Leu His Ile Phe Lys Cys Ser Ala Arg Leu Lys Glu
    210                 215                 220

Asn Ile Asp Glu Val Phe Glu Thr Ala Ile His Thr Leu Leu Ser Asp
225                 230                 235                 240

Ser Leu Tyr Ala Pro Arg Glu Pro Thr His Thr Ile Lys Asn Pro Phe
            245                 250                 255

Lys Arg Asn Thr Thr Ser Gln Tyr Arg Phe Phe Tyr Trp Arg Tyr Gln
            260                 265                 270

Arg Leu Tyr Phe Arg Asn Glu Lys Ile Lys Lys Lys Gln Val Tyr Tyr
        275                 280                 285

Asn Val Arg Ile Met Met Lys Ile Ile Leu Leu Pro Ile Leu Tyr Ala
290                 295                 300

Leu Thr Thr Phe Glu Lys Trp Gln Glu Lys Ile His Thr Phe Tyr Glu
305                 310                 315                 320

Gln Phe Glu Phe Ser Phe Phe Phe Glu Asn Ser Asp Asn Lys Val
            325                 330                 335

Lys Tyr Lys Ala Tyr Leu Ile Ser Ser Ile Lys Arg Trp Ser Ile Ile
            340                 345                 350

Thr Cys Met Arg Cys Phe Trp Thr Val Gln Lys Ser Ile Phe Lys Ala
            355                 360                 365
```

```
Arg Phe Phe Ala Cys Arg Asn Phe Val Lys Lys His Asn Tyr Lys Leu
    370             375             380
Ile Ser Thr Met Thr Gly Ser Thr Glu Met Val Pro Pro Thr Met Lys
385             390             395                         400
His Thr Val Asp Asn Lys Arg Leu Ser Ser Pro Leu Thr Asp Ser Gly
            405             410                     415
Asn Arg Arg Thr Lys Lys Pro Lys Leu Arg Lys Tyr Lys Ala Lys Lys
            420             425             430
Val Glu Thr Thr Ser Pro Met Gly Val Leu Glu Phe Glu Val Asn Asp
        435             440             445
Leu Leu Lys Ser Gln Asn Leu Ser Arg Glu Gln Val Leu Asn Asp Val
    450             455             460
Thr Ser Ile Leu Asn Asp Lys Ser Ser Thr Asp Gly Pro Ile Val Leu
465             470             475                         480
Gln Tyr His Arg Glu
            485
```

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An isolated DNA segment coding for a polypeptide having an amino acid sequence corresponding to RhoNUC wherein said polypeptide has deoxyribonuclease activity and the N-terminal sequence of said polypeptide has homology with a human rho/ras onocogene.

2. The isolated DNA segment according to claim 1, wherein said DNA segment has the sequence shown in SEQ ID NO:1, or allelic, mutant, or species variation thereof.

3. The isolated DNA segment accordingly to claim 1, wherein said DNA segment has a mutant variation of the sequence shown in SEQ ID NO:1.

4. The isolated DNA segment according to claim 2, wherein said DNA segment has the sequence shown in SEQ ID NO:1.

5. The isolated DNA segment according to claim 1, wherein said DNA segment encodes the amino acid sequence set forth in SEQ ID NO:2, or allelic or species variation thereof.

6. The isolated DNA segment according to claim 5, wherein said DNA segment encodes the amino acid sequence set forth in SEQ ID NO:2.

7. An isolated recombinant DNA molecule comprising a vector and the DNA segment according to claim 1.

8. An isolated culture of cells that contain the isolated recombinant DNA molecule according to claim 7.

9. An isolated culture of cells containing the RNC1 gene, wherein said RNC1 gene contains a mutation in the region of said gene that encodes an amino acid sequence that confers deoxyribonuclease activity on the protein product encoded by said gene.

10. An isolated culture of cells containing the RNC1 gene, wherein said RNC1 gene contains a mutation in the region of said gene that encodes an amino acid sequence that has homology with a rho/ras oncogene.

11. An isolated DNA segment that contains a gene that suppresses the genetic defect caused by a mutation in the RNC1 gene of a cell having an RNC1 gene, wherein said mutation is in the region of said RNC1 gene that confers deoxyribonuclease activity on the protein product encoded by said gene.

12. An isolated DNA segment that contains a gene that suppresses the genetic defect caused by a mutation in the RNC1 gene of a cell having an RNC1 gene, wherein said mutation is in the region of said RNC1 gene that encodes an amino acid sequence that has homology with a rho/ras oncogene.

* * * * *